(12) United States Patent
Nakaoka et al.

(10) Patent No.: US 6,562,017 B1
(45) Date of Patent: May 13, 2003

(54) ABSORBENT ARTICLE WITH RAISABLE STRIPS

(75) Inventors: Kenji Nakaoka, Tokushima (JP); Masaru Fujioka, Tokushima (JP); Satoshi Maeda, Tokushima (JP); Kazuyo Mori, Tokushima (JP)

(73) Assignee: Livedo Corporation, Ehime (JP)

( * ) Notice: Subject to any disclaimer, the term of this patent is extended or adjusted under 35 U.S.C. 154(b) by 32 days.

(21) Appl. No.: 09/856,432

(22) PCT Filed: Sep. 28, 2000

(86) PCT No.: PCT/JP00/06685

§ 371 (c)(1), (2), (4) Date: May 21, 2001

(87) PCT Pub. No.: WO01/22910

PCT Pub. Date: Apr. 5, 2001

(30) Foreign Application Priority Data

Sep. 30, 1999 (JP) .......................................... 11-279903

(51) Int. Cl.[7] ................................................. A61F 13/20
(52) U.S. Cl. ............................ 604/385.28; 604/385.13; 604/385.01; 604/385.04
(58) Field of Search ....................... 604/385.28, 385.13, 604/385.01

(56) References Cited

U.S. PATENT DOCUMENTS

| | | | | |
|---|---|---|---|---|
| 5,085,654 A | * | 2/1992 | Buell | 604/370 |
| 5,342,342 A | * | 8/1994 | Kitaoka | 604/385.19 |
| 5,542,943 A | * | 8/1996 | Sageser | 604/385.2 |
| 5,662,636 A | * | 9/1997 | Benjamin et al. | 604/385.28 |
| 6,248,098 B1 | * | 6/2001 | Sayama | 604/385.19 |

* cited by examiner

Primary Examiner—Robert M. Fetsuga
Assistant Examiner—Amanda R. Flynn
(74) Attorney, Agent, or Firm—Jordan and Hamburg LLP

(57) ABSTRACT

An absorbent article having raisable strips with inner portions of the raisable strips arranged at the opposite side of the absorbent article being folded to have a Z-shaped cross section. Bottom portions of the Z-shaped inner portions are bonded to a top sheet of the absorbent article, and elastic members are mounted in top portions of the Z-shaped inner portions so that the top portions are raised flat together with slanted side portions of the Z-shaped inner portions.

17 Claims, 5 Drawing Sheets

ABSORBENT ARTICLE WITH RAISABLE STRIPS

FIELD OF THE INVENTION

The present invention relates to an absorbent article used for a disposable diaper or the like which has a good fit for a wearer and can securely prevent a lateral leak of urine or other liquid bodily waste.

BACKGROUND OF THE INVENTION

An absorbent article used for a disposable diaper or the like includes an absorbent core arranged between its back sheet and top sheet and raisable strips having inner portions for covering the opposite sides of the upper surface of the absorbent article arranged at the opposite sides of the absorbent article.

Since elastic members are mounted in an extended state at the leading ends of the raisable strips, the raisable strips raise and form banks when the disposable diaper is used, and the elastic members thereof are brought into contact with the skin surface of a user or wearer, thereby preventing a lateral leak of urine or other liquid bodily waste.

However, since the elastic members of the raisable strips extend straight along the forward and backward directions of the absorbent article, the raisable strips are only linearly brought into contact with the skin surface of the wearer, presenting problem of a poor fit and an inability to securely prevent a lateral leak of urine or other liquid bodily waste.

In view of the problems in the prior art absorbent articles, an object of the present invention is to provide an absorbent article which has a good fit for a wearer and can securely prevent a lateral leak of urine or other liquid bodily waste.

SUMMARY OF THE INVENTION

The present invention is directed to an absorbent article for use in a disposable diaper or the like, which comprises an absorbent core arranged between a back sheet and a top sheet, and raisable strips provided on the opposite sides of the absorbent article so that inner edge portions thereof cover the opposite sides of the upper surface of the absorbent article. Inner portions of the raisable strips are folded to have a Z-shaped cross section. Bottom portions of the Z-shaped inner portions are bonded to the top sheet of the absorbent article and elastic members are mounted in top portions of the inner portions so that the top portions are raised flat together with slanted side portions situated between the top and bottom portions.

In accordance with the invention, the top portions can be raised flat together with the slanted side portions by folding the inner portions of the raisable strips to have a Z-shaped cross section, bonding the bottom portions of the Z-shaped inner portions to the top sheet of the absorbent article, and mounting the elastic members in the top portions.

Elastic ribbons or elastic threads may be used as the elastic members.

Preferably, outer portions of the raisable strips are bonded to the back sheet of the absorbent article. In this manner, the raisable strips can be of the unit type integral to the absorbent article.

Preferably, the slanted side portions and the top portions at the front and rear parts of the inner portions of the raisable strips are bonded to the top sheet of the absorbent article, and unbonded intermediate portions between the front and rear parts are 40% or more of the entire length of the absorbent article.

Preferably, the unbonded intermediate portions are displaced forward by 5% or more with respect to the center of the entire length of the absorbent article.

DETAILED DESCRIPTION OF THE INVENTION

Hereinafter, embodiments of the present invention are described in detail with reference to the accompanying drawings.

Figure 1:
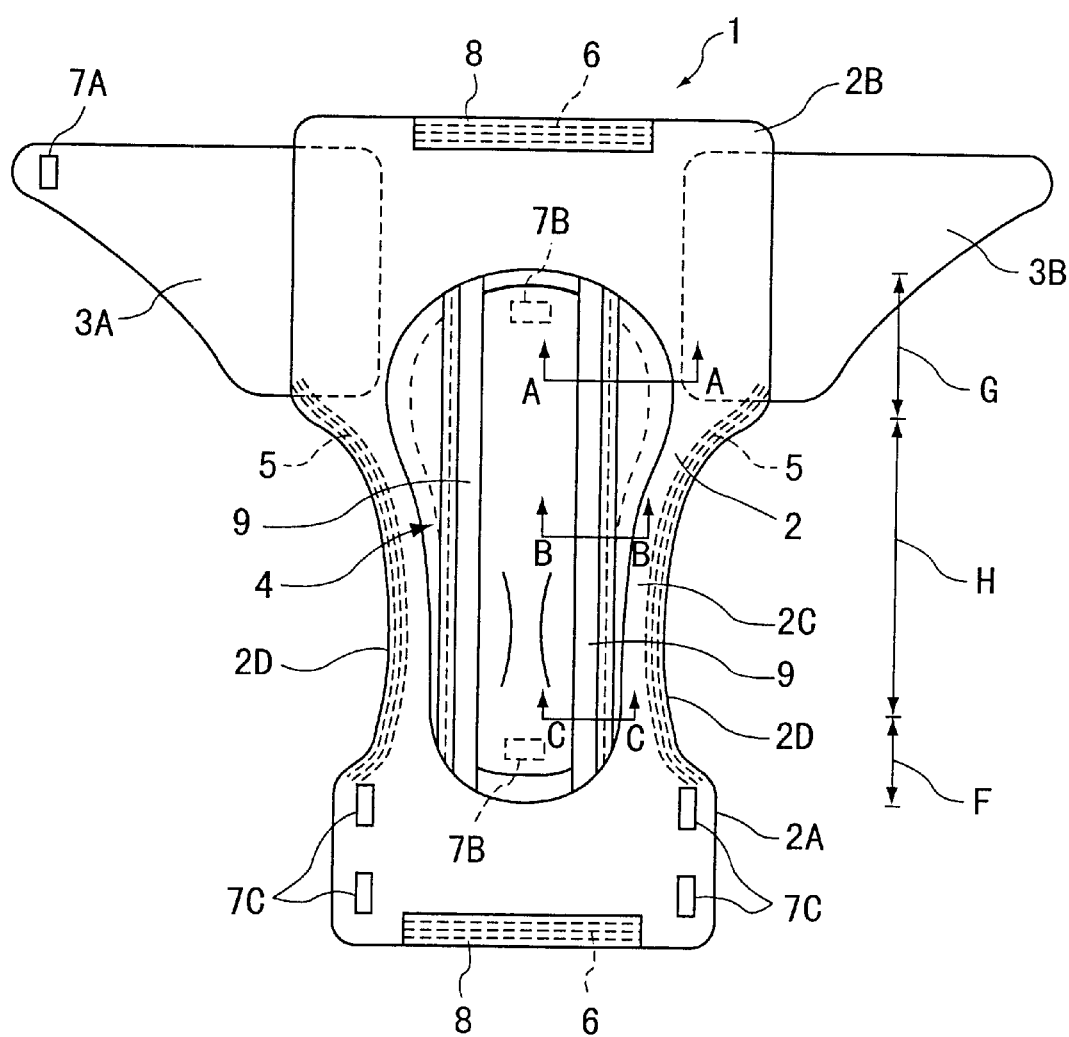
FIG. 1 is a front view of a unfolded state of a disposable diaper using an absorbent article in accordance with the invention.
Figure 2:
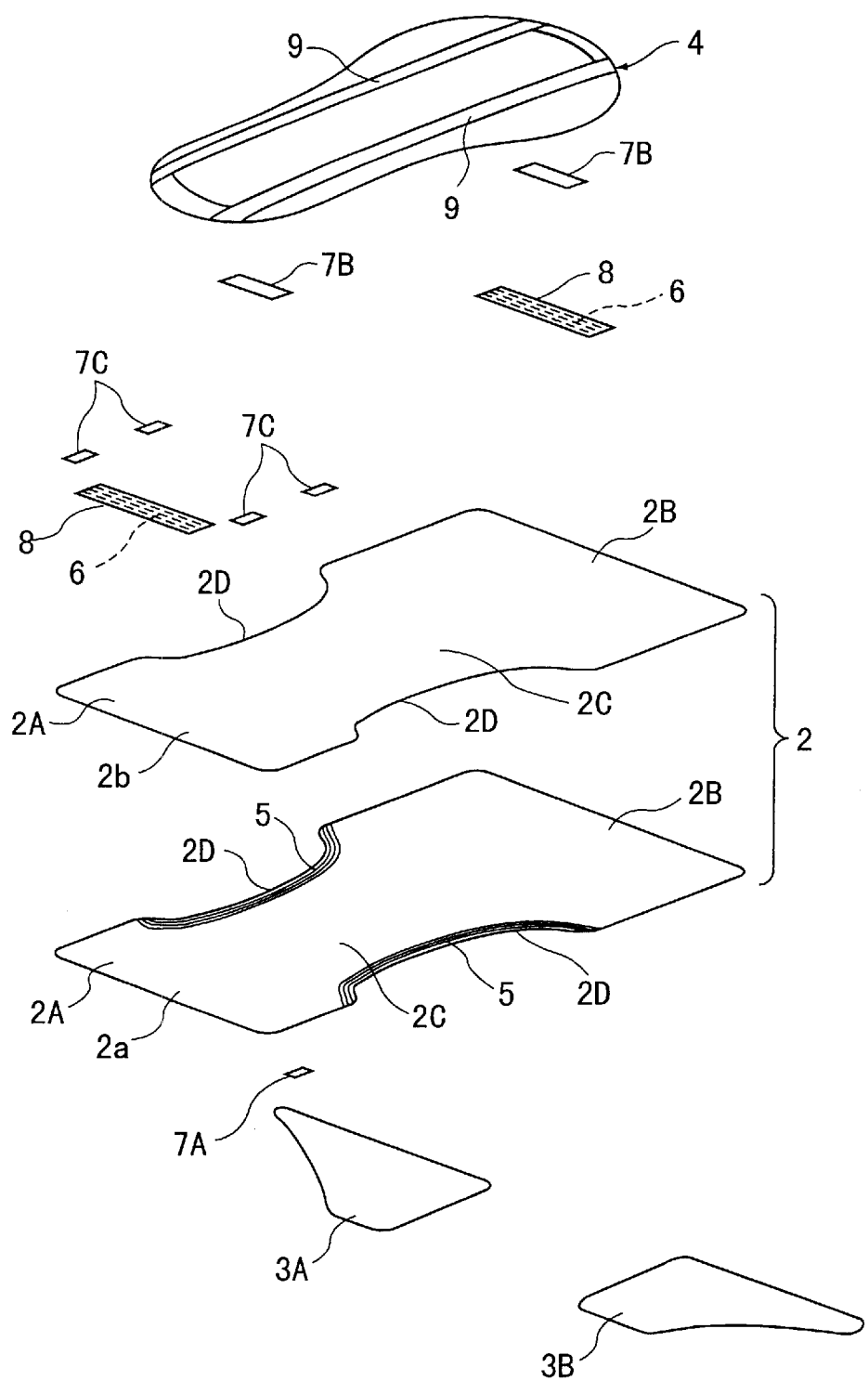
FIG. 2 is an exploded perspective view of parts of the disposable diaper using the absorbent article in accordance with the invention.

As shown in FIGS. 1 and 2, a disposable diaper 1 comprises a covering portion 2 having a front section 2A, a crotch section 2C and a rear section 2B, a pair of waist fastening strip portions 3 (A, B) arranged at the opposite sides of the rear section 2B of the covering portion 2, and an absorbent article 4 which is arranged to extend from the crotch section 2C over to the front section 2A and the rear section 2B on the skin side of the covering portion 2.

The covering portion 2 includes an impermeable outer sheet 2a formed of a plastic film which is liquid-impermeable and a permeable skin side sheet 2b formed of a soft-touch nonwoven fabric of synthetic fibers. The outer sheet 2a may be a permeable nonwoven fabric made of synthetic fibers. After a plurality of elastic threads 5 for leg stretchable gathers are intermittently adhered around leg-openings 2D of the crotch section 2C of the impermeable outer sheet 2a while being extended in longitudinal direction, the permeable skin side sheet 2b on the skin side is bonded to the impermeable outer sheet 2a by melting or adhesion. The permeable skin side sheet 2b has an outer surface configuration which serves as a loop-like locking portion of the mechanical fastener as described later.

Strip sheets 8 in which a plurality of elastic threads 6 are intermittently adhered while being extended in longitudinal direction for waist stretchable gathers are bonded to upper parts of the inner surfaces of the front section 2A and the rear section 2B of the permeable sheet 2b of the covering portion 2 by melting or adhesion.

The elastic threads 5 for leg gathers and the elastic threads 6 for waist gathers are made of ribbons or threads of natural or synthetic rubber, polyurethane or like material, and the waist stretchable gathers and the leg stretchable gathers can be naturally formed by the shrinkage of the respective elastic threads 5, 6.

The pair of waist fastening strip portions 3 (A, B) are made of a knitted web or a nonwoven fabric of synthetic fibers having an outer surface configuration which serves as a loop-like locking portion of a mechanical fastener.

The mechanical fastener is such that a hook-like locking portion (male locking portion) and a loop-like locking portion (female locking portion) are provided in a pair, the male and female locking portions are locked into each other when being strongly pressed against each other while being disengaged from each other when being strongly pulled apart by hands. This fastener is also called a "velcro" (trade mark) fastener. Instead of the mechanical fastener, separable adhesive may be used.

The pair of waist fastening strip portions 3 (A, B) are each formed into a substantially triangular shape. The bottom portion of the each triangular shaped portion 3 (A, B) jointed to the opposite sides of the back surface of the rear section 2B of the covering portion 2 (namely, the back side of the impermeable outer sheet 2a) by melting or adhesion. Each apex portion thereof is projected outwardly.

On the inner surface of one waist fastening strip portion 3A, a hook-like first locking member 7A of a mechanical fastener is arranged and is detachably locked with the outer surface (loop-like locking portion of a mechanical fastener) of the other waist fastening strip portion 3B.

Figure 5A:
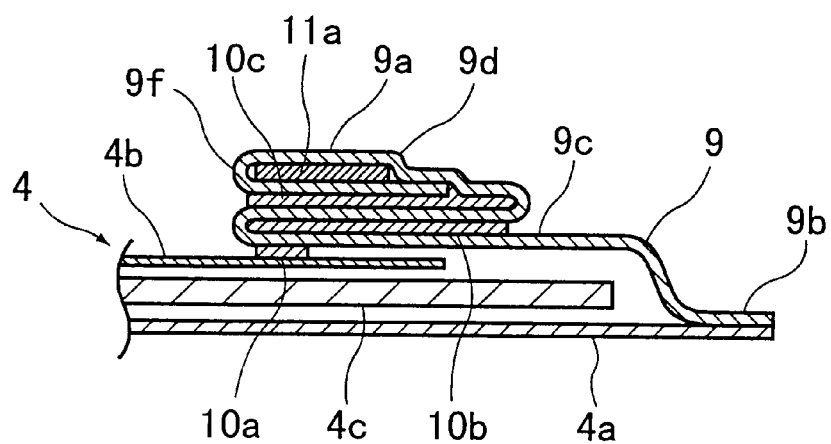
FIG. 5A is an enlarged sectional view taken along the line A—A and the line C—C of FIG. 1.
Figure 5B:
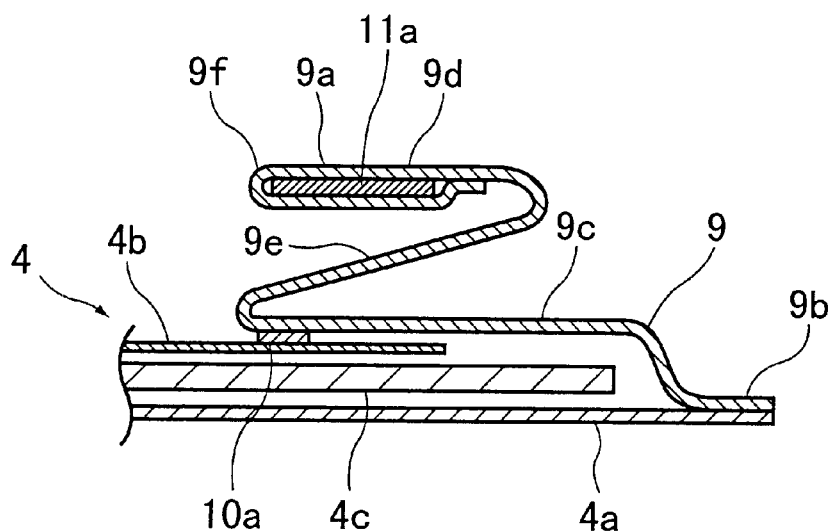
FIG. 5B is an enlarged sectional view taken along the line B—B of FIG. 1.

The absorbent article 4 is formed flat by accommodating an absorbent core 4c made of a mixture of, e.g., pulp fibers, super absorbent polymers between an impermeable back sheet 4a and a permeable top sheet 4b as shown in detail in FIGS. 5A and 5B, has an elliptical shape having a narrow front part and a wider rear part, and is arranged to extend from the crotch section 2C to the front section 2A and the rear section 2B on the skin side of the covering portion 2.

A pair of left and right raisable strips (cuffs) 9 for preventing a lateral leak of urine or other liquid bodily waste are arranged at the opposite sides of the upper surface of the top sheet 4b of the absorbent article 4.

The raisable strips 9 are made of a nonwoven fabric of repellent synthetic fibers. Outer portions 9b have the same arcuate shape as the opposite side portions of the absorbent article 4, straight inner portions 9a cover the opposite sides of the upper surface of the absorbent article 4, and the outer portions 9b are adhered to the upper surface of the back sheet 4a.

The inner portion 9a of each raisable strip 9 is folded to have a Z-shaped cross section, and a bottom portion 9c thereof is adhered to the top sheet 4b of the absorbent article 4 by an adhesive 10a over the entire length of the inner side.

Figure 4:
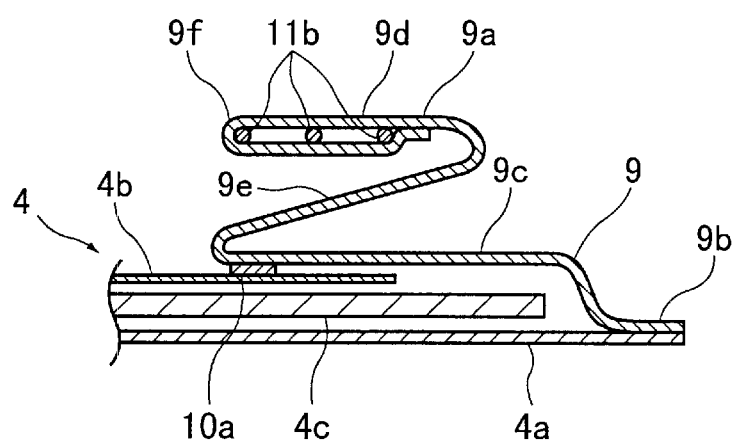
FIG. 4 is an enlarged sectional view taken along the line B—B of FIG. 1 when elastic threads are used.

An end portion 9f of a top portion 9d of the inner portion 9a is folded down, and an elastic ribbon 11a extending in forward and backward directions is adhered to the folded portion. The elastic ribbon 11a is made of natural rubber or synthetic rubber so that stretchable gathers are naturally formed at the end portion 9f of the top portion 9d by the shrinking force of the elastic ribbon 11a. As shown in FIG. 4, a plurality of elastic threads 11b may be adhered instead of the elastic ribbon 11a.

As shown in FIG. 1, the lower surfaces of slanted side portions 9e located in a specified front area F and a specified rear area G of the inner portions 9a of the raisable strips 9 are adhered to the upper surfaces of the bottom portions 9c by an adhesive 10b, and the lower surfaces of the top portions 9d are adhered to the upper surfaces of the slanted side portions 9e by an adhesive 10c. In other words, the slanted side portions 9e and the top portions 9d in the respective areas F, G are bonded to the top sheet 4b of the absorbent article 4.

An unbonded intermediate area H between the respective areas F, G is preferably 40% or more of the entire length of the absorbent article 4, and this intermediate area H is preferably displaced forward by 5% or more from the center of the entire length of the absorbent article 4. The former construction ensures a satisfactory fit with the wearer since the raisable strips are raised over a sufficient length, whereas the latter construction betters the fit of the raisable strips at the front.

The top portions 9d are raised flat together with the slanted side portions 9e when the disposable diaper 1 is used as shown in FIG. 5B by folding the inner portions 9a of the raisable strips 9 to have a Z-shaped cross section, adhering the entire bottom portions 9c to the top sheet 4b of the absorbent article 4, adhering the front and rear areas F. G of the top portions 9d and the slanted side portions 9e to the top sheet 4b, and adhering the elastic ribbons 11a or elastic threads 11b to the end portions 9f of the top portions 9d.

On the other hand, hook-like second locking members 7B of the mechanical fasteners which are detachably locked with the permeable skin side sheet 2b (loop-like locking portion of the mechanical fastener) of the covering portion 2 are mounted on the respective rear surfaces of the front and rear ends of the absorbent article 4. The hook-like second locking member 7B may be mounted in a position of the absorbent article 4 other than the above, e.g., at the crotch section.

Hook-like locking portions 7C of the mechanical fasteners which are detachably locked with the outer surfaces (loop-like locking portion of the mechanical fasteners) of the pair of waist fastening strip portions 3 (A, B) are mounted on the opposite sides of the skin surface of the front section 2A of the covering portion 2.

The disposable diaper 1 thus constructed is used or worn as follows. With the disposable diaper 1 in its developed state, the front and rear sides of the absorbent article 4 are locked to the front and rear sides of the covering portion 2 by the hook-like locking members 7B, the rear section 2B of the covering portion 2 is placed under the back of a wearer and, while the other waist fastening strip portion 3B is folded to the front to be placed on the wearer's abdomen, the one waist fastening strip portion 3A is folded to the front to be locked to the outer surface of the other waist fastening strip portion 3B by the hook-like first locking member 7A.

Figure 3:
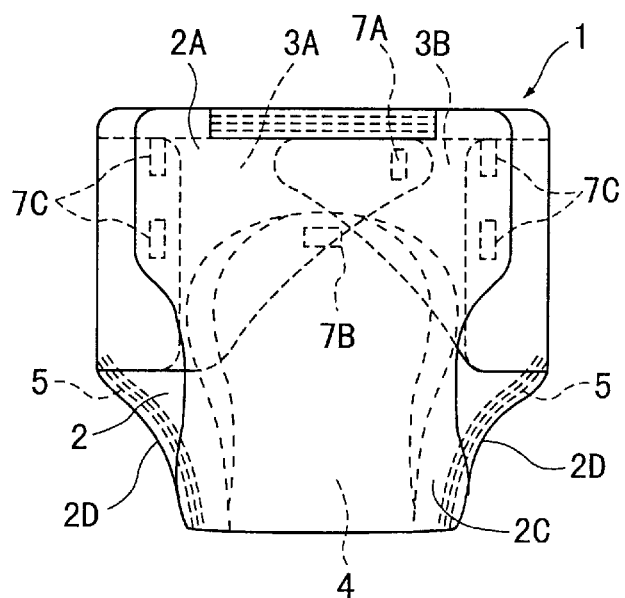
FIG. 3 is a front view of the disposable diaper in its worn state.

Subsequently, the front section 2A of the covering portion 2 is folded to the front through the crotch of the wearer to place the absorbent article 4 on his crotch, and is then locked to the pair of waist fastening strip portions 3(A, B) by the hook-like third locking members 7C. In this way, the disposable diaper 1 is completely worn in such a state as shown in FIG. 3.

In the above disposable diaper 1, the top portions 9d are raised flat together with the slanted side portions 9e and come into surface contact with the skin surface at the wearer's crotch in forward and backward directions by folding the inner portions 9a of the raisable strips 9 provided at the opposite sides of the absorbent article 4 to have a Z-shaped cross section, adhering the bottom portions 9c to the top sheet 4b of the absorbent article 4, and mounting the elastic ribbons 11a or elastic threads 11b in the top portions 9d. This improves the fit and, therefore, can securely prevent a lateral leak of urine or other liquid bodily waste.

It should be appreciated that the absorbent article 4 and the covering portion 2 may be formed integral to each other in the disposable diaper 1 as in the prior art instead of separating them.

Figure 6A:
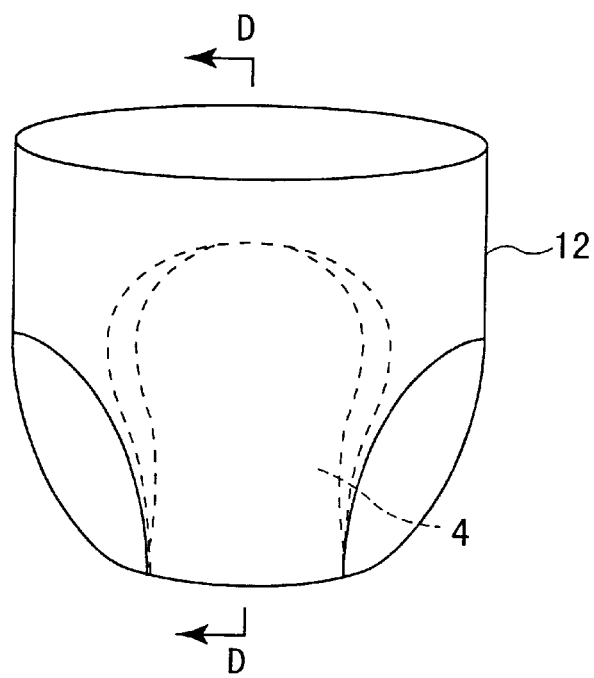
FIG. 6A is a perspective view of disposable underpants using the absorbent article.
Figure 6B:
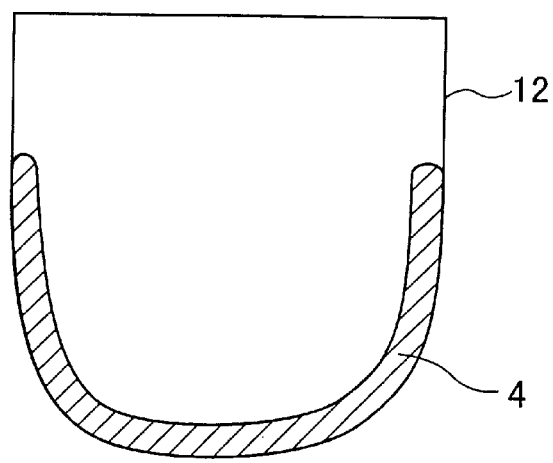
FIG. 6B is a sectional view taken along the line D—D of FIG. 6A.

Although the absorbent article 4 is used in the disposable diaper 1 in the foregoing embodiment, it may be used by being directly adhered to pants 12 as a sanitary napkin as shown in FIGS. 6A and 6B.

As is clear from the above description, according to the invention, the top portions can be raised flat together with the slanted side portions by folding the inner portions of the raisable strips to have a Z-shaped cross section, bonding the bottom portions of the Z-shaped inner portions to the top sheet of the absorbent article, and mounting the elastic members in the top portions. Thus, the top portions of the inner portions of the raisable strips are brought into surface contact with the skin surface of the wearer in forward and backward directions, which improves the fit and, therefore, can securely prevent a lateral leak of urine or other liquid bodily waste.

When the outer portions of the raisable strips are bonded to the back sheet of the absorbent article, the raisable strips can be of the unit integral to the absorbent article.

When the slanted side portions and the top portions at the front and rear parts of the inner portions of the raisable strips are bonded to the top sheet of the absorbent article, and the unbonded intermediate portions between the front and rear parts are 40% or more of the entire length of the absorbent article, the raisable strips are raised over a sufficient length to improve fittability.

When the unbonded intermediate portions are displaced forward by 5% or more with respect to the center of the entire length of the absorbent article, the fit of the raisable strips at the front is better.

As described above, since the inventive absorbent article securely prevents a lateral leak of urine or other liquid bodily waste, it can be used as it is as a urine absorbing pad or can be used in a disposable product such as a disposable diaper or disposable pants.

What is claimed is:

1. An absorbent article for use in a disposable diaper, comprising:
    a top sheet,
    a back sheet,
    an absorbent core arranged between said back sheet and said top sheet, and
    raisable strips each arranged on a respective side of said absorbent core such that inner edge portions of said raised strips cover an upper surface of said top sheet,
    each of said raisable strips having an inner portion folded to have a Z-shaped cross section,
    said inner Z-shaped portion having a bottom portion bonded to said top sheet, a top portion and a slanted side portion arranged between said top portion and said bottom portion,
    each of said raisable strips further including elastic members mounted in said top portion such that said top portion is raisable together with said slanted side portion relative to said bottom portion, and
    wherein said elastic members are adhered to a free end portion of said top portion.

2. An absorbent article according to claim 1, wherein said elastic members are elastic ribbons or elastic threads.

3. An absorbent article according to claim 1 or 2, wherein each of said raisable strips has an outer portion bonded to said back sheet.

4. An absorbent article according to claim 1, wherein said slanted side portions and said top portions at front and rear parts of said inner portions of said raisable strips are bonded to said top sheet, and unbonded intermediate portions between said front and rear parts are 40% or more of the entire length of the absorbent article.

5. An absorbent article according to claim 4, wherein said unbonded intermediate portions are displaced forward by 5% or more with respect to the center of the entire length of the absorbent article.

6. An absorbent article according to claim 1, wherein said raisable strips are arranged at opposite sides of said upper surface of said top sheet.

7. An absorbent article according to claim 1, wherein said top portion of each of said raisable strips includes an end portion folded over and re-contacting said top portion.

8. An absorbent article according to claim 7, wherein said elastic members are arranged between said end portion of said top portion and a remaining portion of said top portion.

9. An absorbent article according to claim 7, wherein said end portion of said top portion faces said slanted side portion.

10. An absorbent article according to claim 1, wherein said raisable strips are made of a non-woven fabric.

11. An absorbent article according to claim 1, wherein said raisable strips are made of a non-woven fabric of synthetic fibers.

12. An absorbent article according to claim 1, wherein said slanted side portion is inclined from an inner region of said bottom portion to an outer region of said top portion.

13. An absorbent article according to claim 1, further comprising an adhesive for attaching said bottom portion to said upper surface of said top sheet.

14. An absorbent article according to claim 1, wherein only a part of said slanted side portions and a part of said top portions over the length of said raisable strips are bonded to said top sheet such that remaining parts of said slanted side portions and remaining parts of said top portions are not bonded to said top sheet.

15. An absorbent article according to claim 14, wherein said unbonded remaining parts are displaced forward by 5% or more with respect to the center of the entire length of the absorbent article.

16. An absorbent article according to claim 1, wherein said top sheet is smaller than said back sheet such that edges of said absorbent core are exposed, said raisable strips covering the exposed portions of said absorbent core.

17. An absorbent article according to claim 1, wherein said top sheet is permeable and said back sheet is impermeable.

* * * * *